United States Patent
Douglas et al.

(10) Patent No.: US 12,380,628 B1
(45) Date of Patent: Aug. 5, 2025

(54) METHOD AND APPARATUS FOR GENERATING A COLORED THREE DIMENSIONAL VOLUME VIA VOXEL ELIMINATION AND COLOR ASSIGNMENT TO VOXEL GROUPS

(71) Applicant: D3D Technologies, Inc., Orlando, FL (US)

(72) Inventors: Robert Edwin Douglas, Winter Park, FL (US); David Byron Douglas, Winter Park, FL (US)

(73) Assignee: D3D Technologies, Inc., Orlando, FL (US)

( * ) Notice: Subject to any disclaimer, the term of this patent is extended or adjusted under 35 U.S.C. 154(b) by 0 days.

(21) Appl. No.: 17/728,903

(22) Filed: Apr. 25, 2022

Related U.S. Application Data

(63) Continuation of application No. 17/459,939, filed on Sep. 26, 2021, now Pat. No. 11,315,307, which is a
(Continued)

(51) Int. Cl.
*H04N 7/18* (2006.01)
*G06T 15/08* (2011.01)
(Continued)

(52) U.S. Cl.
CPC .............. *G06T 15/08* (2013.01); *G06T 15/20* (2013.01); *H04N 13/344* (2018.05); *G06T 2210/41* (2013.01)

(58) Field of Classification Search
CPC ..................................................... G06T 15/08
(Continued)

(56) References Cited

U.S. PATENT DOCUMENTS

| 4,991,092 A | * | 2/1991 | Greensite | G06T 5/10 |
| | | | | 382/274 |
| 5,488,952 A | | 2/1996 | Schoolman | |

(Continued)

FOREIGN PATENT DOCUMENTS

| EP | 1056049 A2 * | 11/2000 | ............ G06T 15/08 |
| WO | WO-9613207 A1 * | 5/1996 | ............ A47B 81/06 |
| WO | WO-2007059477 A2 * | 5/2007 | ............ G06T 19/00 |

OTHER PUBLICATIONS

Defendant Microsoft Corporation's Supplemental Invalidity Contentions for *D3D Technologies, Inc. v. Microsoft Corporation*; U.S. District Court Middle District of Florida Orlando Division; Case No. 6:20-CV-1699-PGB-DCI; Entered Apr. 19, 2021 (5 Pages).
(Continued)

*Primary Examiner* — Leron Beck
(74) *Attorney, Agent, or Firm* — Almanac IP Advisors LLP

(57) ABSTRACT

Pointers are added to a 3D volumetric dataset to help the user visualize the direction of blood flow. A 3D volume containing at least one blood vessel is created. Next, the direction of the blood flow is determined. Next, at least pointer is placed into the 3D volume in an aligned fashion with the direction of blood flow such that the 3D volume is modified. Next, the modified 3D volume is displayed on a head display unit, such as an augmented reality or virtual reality display. Next, at least one pointer is advanced to a new position for additional modification of the 3D imaging volume.

28 Claims, 6 Drawing Sheets

Related U.S. Application Data continuation of application No. 16/506,073, filed on Jul. 9, 2019, now Pat. No. 11,202,061, which is a continuation-in-part of application No. 15/878,463, filed on Jan. 24, 2018, now Pat. No. 10,795,457, which is a continuation-in-part of application No. 14/877,442, filed on Oct. 7, 2015, now Pat. No. 9,980,691, which is a continuation-in-part of application No. 12/176,569, filed on Jul. 21, 2008, now Pat. No. 9,349,183, which is a continuation-in-part of application No. 11/941,578, filed on Nov. 16, 2007, now Pat. No. 8,384,771.

(60) Provisional application No. 60/877,931, filed on Dec. 28, 2006.

(51) Int. Cl.
*G06T 15/20* (2011.01)
*H04N 13/344* (2018.01)

(58) Field of Classification Search
USPC .......................................................... 348/494
See application file for complete search history.

(56) References Cited

U.S. PATENT DOCUMENTS

| | | | | |
|---|---|---|---|---|
| 5,523,886 | A * | 6/1996 | Johnson-Williams | A63F 13/26 359/464 |
| 5,535,747 | A * | 7/1996 | Katakura | A61B 8/04 600/438 |
| 5,630,034 | A * | 5/1997 | Oikawa | G06T 15/08 345/424 |
| 5,875,055 | A * | 2/1999 | Morishima | H04N 13/315 348/E13.043 |
| 5,986,662 | A * | 11/1999 | Argiro | G06T 11/00 345/422 |
| 6,016,439 | A * | 1/2000 | Acker | A61B 90/36 600/414 |
| 6,108,005 | A * | 8/2000 | Starks | G02B 30/23 348/42 |
| 6,501,468 | B1 * | 12/2002 | Kaji | H04N 13/341 348/E13.059 |
| 6,658,080 | B1 * | 12/2003 | Poole | G06T 19/20 378/94 |
| 6,847,336 | B1 * | 1/2005 | Lemelson | H04N 7/147 345/8 |
| 8,384,771 | B1 * | 2/2013 | Douglas | H04N 13/344 348/42 |
| 9,349,183 | B1 * | 5/2016 | Douglas | G02B 27/017 |
| 2004/0109139 | A1 * | 6/2004 | Kiser | G02B 27/149 353/31 |
| 2005/0168461 | A1 * | 8/2005 | Acosta | G06T 19/00 345/419 |
| 2005/0240094 | A1 * | 10/2005 | Pichon | G06T 19/20 600/407 |
| 2006/0181482 | A1 * | 8/2006 | Iaquinto | A61B 90/36 345/8 |
| 2006/0210147 | A1 * | 9/2006 | Sakaguchi | G01C 11/06 348/42 |
| 2006/0241458 | A1 * | 10/2006 | Hayashi | A61B 8/06 600/453 |
| 2007/0012101 | A1 * | 1/2007 | Rottger | G06T 7/187 73/170.24 |
| 2007/0071311 | A1 * | 3/2007 | Rovira-Mas | G06T 7/70 382/104 |
| 2007/0263915 | A1 * | 11/2007 | Mashiach | G06V 10/267 382/130 |
| 2007/0276214 | A1 * | 11/2007 | Dachille | G16H 30/40 600/407 |
| 2010/0081912 | A1 * | 4/2010 | McKenna | A61B 5/1455 600/368 |
| 2011/0196237 | A1 * | 8/2011 | Pelissier | A61B 8/543 600/454 |
| 2014/0307067 | A1 * | 10/2014 | Douglas | H04N 13/344 348/53 |
| 2015/0379351 | A1 * | 12/2015 | Dibenedetto | G02B 27/017 345/633 |
| 2018/0116728 | A1 * | 5/2018 | Lang | A61B 17/1764 |
| 2018/0168740 | A1 * | 6/2018 | Ryan | A61B 90/36 |

OTHER PUBLICATIONS

Defendant Microsoft Corporation's Fifth Supplemental Invalidity Contentions for *D3D Technologies, Inc.* v. *Microsoft Corporation*; U.S. District Court Middle District of Florida Orlando Division; Case No. 6:20-Cv-1699-PGB-DCI; Entered Jan. 10, 2022 (23 Pages).

Moreira et al. 3D Markup of Radiological Images in ePAD, a Web-Based Image Annotation Tool; 2015 IEEE 28th International Symposium on Computer-Based Medical Systems, (6 pages).

Exhibit B: "U.S. Pat. No. 9,980,691 is Anticipated by and/or Rendered Obvious In View of Moreira" Invalidity Chart Based on Microsoft Corporation's Supplemental Invalidity Contentions for *D3D Technologies, Inc.* v. *Microsoft Corporation*; U.S. District Court Middle District of Florida Orlando Division; Case No. 6:20-Cv-1699-Gap-Dci; Entered Apr. 19, 2021 (68 Pages).

Exhibit C: "U.S. Pat. No. 10,795,457 is Anticipated by and/or Rendered Obvious In View of Moreira" Invalidity Chart Based on Microsoft Corporation's Supplemental Invalidity Contentions for *D3D Technologies, Inc.* v. *Microsoft Corporation*; U.S. District Court Middle District of Florida Orlando Division; Case No. 6:20-Cv-1699-Gap-Dci; Entered Apr. 19, 2021 (64 Pages).

IPR2021-00647 Final Written Decision in *Microsoft Corporation* v. *D3D Technologies, Inc.*; United States Patent and Trademark Office— Before the Patent Trial and Appeal Board, Case No. IPR2021-00647; Entered Aug. 3, 2022 (31 pages).

IPR2021-00647 Petition for Inter Partes Review of U.S. Pat. No. 8,384,771 Pursuant to 35 U.S.C. §§ 311-319, 37 C.F.R. § 42; United States Patent and Trademark Office—Before the Patent Trial and Appeal Board, Case No. IPR2021-00647, filed Mar. 23, 2021 (112 pages).

IPR2021-00647 Petitioner's Reply to Patent Owner's Response in *Microsoft Corporation* v. *D3D Technologies, Inc.*; United States Patent and Trademark Office—Before the Patent Trial and Appeal Board, Case No. IPR2021-00647; Entered on Feb. 23, 2022 (29 pages).

United States Court of Appeals for the Federal Circuit; Case No. 23-1011; Appeal from the United States Patent and Trademark Office, Patent Trial and Appeal Board in No. IPR2021-00647; *Microsoft Corporation* v. *D3D Technologies, Inc.*; Decided Feb. 20, 2024 (8 pages).

U.S. Appl. No. 18/049,272 Non-Final Office Action dated Dec. 19, 2023 (69 pages).

U.S. Appl. No. 18/049,272 Final Office Action dated Aug. 23, 2024 (78 pages).

Exhibit C-1: "U.S. Pat. No. 8,384,771 is Anticipated By and/or Rendered Obvious In View of the View system" from Defendant Microsoft Corporation's Third Supplemental Invalidity Contentions for *D3D Technologies. Inc.* v. *Microsoft Corporation*; U.S. District Court, Middle District of Florida Orlando Division; Case No. 6:20-cv-1699-PGB-DCI; Entered Oct. 12, 2021 (101 Pages).

Defendant Microsoft Corporation's Preliminary Invalidity Contentions for *D3D Technologies. Inc.* v. *Microsoft Corporation*; U.S. District Court Middle District of Florida Orlando Division; Case No. 6:20-Cv-1699-Gap-Dci; Entered Feb. 4, 2021 (158 Pages).

Defendant Microsoft Corporation's Second Supplemental Invalidity Contentions for *D3D Technologies. Inc.* v. *Microsoft Corporation*; U.S. District Court, Middle District of Florida Orlando Division; Case No. 6:20-cv-1699-PGB-DCI; Entered Sep. 17, 2021 (14 Pages).

(56) References Cited

OTHER PUBLICATIONS

Defendant Microsoft Corporation's Third Supplemental Invalidity Contentions for *D3D Technologies. Inc.* V. *Microsoft Corporation*; U.S. District Court, Middle District of Florida Orlando Division; Case No. 6:20-cv-1699-PGB-DCI; Entered Oct. 12, 2021 (17 Pages).
Defendant Microsoft Corporation's Fourth Supplemental Invalidity Contentions for *D3D Technologies. Inc.* v. *Microsoft Corporation*; U.S. District Court, Middle District of Florida Orlando Division; Case No. 6:20-cv-1699-PGB-DCI; Entered Nov. 15, 2021 (52 Pages).
Exhibit D-1: "S.S. Fisher, et al., Virtual Environment Display System, Proceedings of the 1986 workshop on Interactive 3D graphics, Jan. 1987, at 77, https://doi.org/10.1145/319120.319127" from Defendant Microsoft Corporation's Third Supplemental Invalidity Contentions for *D3D Technologies. Inc.* v. *Microsoft Corporation*; U.S. District Court, Middle District of Florida Orlando Division; Case No. 6:20-cv-1699-PGB-DCI; Entered Oct. 12, 2021 (12 Pages).
Exhibit D-10: "Scott Fisher, Telepresence in Dataspace NASA Ames VIEWlab, 1987, https://youtu.be/guOUfhoNhDY. ("1987 Demo")" from Defendant Microsoft Corporation's Third Supplemental Invalidity Contentions for *D3D Technologies. Inc.* v. *Microsoft Corporation*; U.S. District Court, Middle District of Florida Orlando Division; Case No. 6:20-cv-1699-PGB-DCI; Entered Oct. 12, 2021.
Exhibit D-11: "Scott Fisher, NASA Ames VIEWlab VR demo reel 1989, https://youtu.be/3L0N7CKvOBA ("1989 Demo")" from Defendant Microsoft Corporation's Third Supplemental Invalidity Contentions for *D3D Technologies. Inc.* v. *Microsoft Corporation*; U.S. District Court, Middle District of Florida Orlando Division; Case No. 6:20-cv-1699-PGB-DCI; Entered Oct. 12, 2021.
Exhibit D-12: "ACM SIGCHI, View: The Ames Virtual Environment Workstation, https://youtu.be/H0EI6KLnnSE ("1990 Demo")" from Defendant Microsoft Corporation's Third Supplemental Invalidity Contentions for *D3D Technologies. Inc.* v. *Microsoft Corporation*; U.S. District Court, Middle District of Florida Orlando Division; Case No. 6:20-cv-1699-PGB-DCI; Entered Oct. 12, 2021.
Exhibit D-2: "S.S. Fisher, E.M. Wenzel, C. Coler, M.W. McGreevy, Virtual Interface Environment Workstations, 32 Proc. Hum. Factors Soc'y Ann. Meeting, Feb. 1988, at 91, http://doi.org/10.1177/154193128803200219" from Defendant Microsoft Corporation's Third Supplemental Invalidity Contentions for *D3D Technologies. Inc.* v. *Microsoft Corporation*; U.S. District Court, Middle District of Florida Orlando Division; Case No. 6:20-cv-1699-PGB-DCI; Entered Oct. 12, 2021 (7 Pages).
Exhibit D-3: "A New Continent of Ideas, Spinoff 1990, Jan. 1, 1990, at 88, https://ntrs.nasa.gov/citations/20020086961" from Defendant Microsoft Corporation's Third Supplemental Invalidity Contentions for *D3D Technologies. Inc.* v. *Microsoft Corporation*; U.S. District Court, Middle District of Florida Orlando Division; Case No. 6:20-cv-1699-PGB-DCI; Entered Oct. 12, 2021 (5 Pages).
Exhibit D-4: "Scott S. Fisher, Virtual Environments, Personal Simulation & Telepresence, in Virtual Reality: Theory, Practice and Promise (S. Helsel and J.Roth, ed., Meckler Publishing, 1991)" from Defendant Microsoft Corporation's Third Supplemental Invalidity Contentions for *D3D Technologies. Inc.* v. *Microsoft Corporation*; U.S. District Court, Middle District of Florida Orlando Division; Case No. 6:20-cv-1699-PGB-DCI; Entered Oct. 12, 2021 (8 Pages).
Exhibit D-5: "Steven D. Pieper et al., A Virtual Environment System for Simulation of Leg Surgery, Proc. SPIE 1457, Stereoscopic Displays and Applications II, Aug. 1, 1991, at 188, https://doi.org/10.1117/12.46307 ("Pieper 1991")" from Defendant Microsoft Corporation's Third Supplemental Invalidity Contentions for *D3D Technologies. Inc.* v. *Microsoft Corporation*; U.S. District Court, Middle District of Florida Orlando Division; Case No. 6:20-cv-1699-PGB-DCI; Entered Oct. 12, 2021 (12 Pages).
Exhibit D-6: "Richard H. Jacoby and Stephen R. Ellis, Using Virtual Menus in a Virtual Environment, Proc. SPIE 1668, Visual Data Interpretation, (Jun. 1, 1992); https://doi.org/10.1117/12.59654 ("Jacoby 1992")" from Defendant Microsoft Corporation's Third Supplemental Invalidity Contentions for *D3D Technologies. Inc.* v. *Microsoft Corporation*; U.S. District Court, Middle District of Florida Orlando Division; Case No. 6:20-cv-1699-PGB-DCI; Entered Oct. 12, 2021 (11 Pages).
Exhibit D-7: "Stephen R. Ellis, What Are Virtual Environments, 14 IEEE Computer Graphics & Applications, Jan. 1994, at 17, https://doi.org/10.1109/38.250914 ("Ellis 1994")" from Defendant Microsoft Corporation's Third Supplemental Invalidity Contentions for *D3D Technologies. Inc.* v. *Microsoft Corporation*; U.S. District Court, Middle District of Florida Orlando Division; Case No. 6:20-cv-1699-PGB-DCI; Entered Oct. 12, 2021 (7 Pages).
Exhibit D-8: "Scott S. Fisher, The NASA Ames VIEWlab Project—A Brief History, 25 Presence 339 (2016), https://doi.org/10.1162/PRES_a_00277 ("Fisher 2016")" from Defendant Microsoft Corporation's Third Supplemental Invalidity Contentions for *D3D Technologies. Inc.* v. *Microsoft Corporation*; U.S. District Court, Middle District of Florida Orlando Division; Case No. 6:20-cv-1699-PGB-DCI; Entered Oct. 12, 2021 (11 Pages).
Exhibit D-9: "MDx media, NASA Ames—virtual environment display system, NASA's research into VR from the 1980s, https://youtu.be/gd6_eojjTMU ("1985 Demo")" from Defendant Microsoft Corporation's Third Supplemental Invalidity Contentions for *D3D Technologies. Inc.* v. *Microsoft Corporation*; U.S. District Court, Middle District of Florida Orlando Division; Case No. 6:20-cv-1699-PGB-DCI; Entered Oct. 12, 2021.
Exhibit A-1: "U.S. Pat. No. 8,384,771 Invalidity Chart Based On The Siemens 3D Prior Art System" from Defendant Microsoft Corporation's Third Supplemental Invalidity Contentions for *D3D Technologies. Inc.* v. *Microsoft Corporation*; U.S. District Court, Middle District of Florida Orlando Division, Case No. 6:20-cv-1699-PGB-DCI; Entered Oct. 12, 2021 (72 Pages).
Exhibit B-3: "Siemens, Operating Instructions, InSpace3Dflash, Neurostar/Angiostar/Multistar T.O.P./ Plus" from Defendant Microsoft Corporation's Third Supplemental Invalidity Contentions for *D3D Technologies. Inc.* v. *Microsoft Corporation*; U.S. District Court, Middle District of Florida Orlando Division, Case No. 6:20-cv-1699-PGB-DCI; Entered Oct. 12, 2021 (77 Pages).
Exhibit B-4: "Siemens, SCT and MR Workstation, The Power To See It All, 3DVirtuoso" from Defendant Microsoft Corporation's Third Supplemental Invalidity Contentions for *D3D Technologies. Inc.* v. *Microsoft Corporation*; U.S. District Court, Middle District of Florida Orlando Division; Case No. 6:20-cv-1699-PGB-DCI; Entered Oct. 12, 2021 (9 Pages).
Exhibit B-5: "Siemens, 510(k) Summary, Siemens Realtime 3D Software Package" from Defendant Microsoft Corporation's Third Supplemental Invalidity Contentions for *D3D Technologies. Inc.* v. *Microsoft Corporation*; U.S. District Court, Middle District of Florida Orlando Division; Case No. 6:20-cv-1699-PGB-DCI; Entered Oct. 12, 2021 (5 Pages).
Exhibit A-1: "U.S. Pat. No. 8,384,771 Invalidity Chart Based On The 3D Slicer Prior Art System" from Defendant Microsoft Corporation's Fourth Supplemental Invalidity Contentions for *D3D Technologies. Inc.* v. *Microsoft Corporation*; U.S. District Court, Middle District of Florida Orlando Division; Case No. 6:20-cv-1699-PGB-DCI; Entered Nov. 15, 2021 (96 Pages).
Exhibit A-1: "U.S. Pat. No. 8,384,771 Invalidity Chart Based On The 3D Slicer Prior Art System" from Defendant Microsoft Corporation's Fifth Supplemental Invalidity Contentions for *D3D Technologies. Inc.* v. *Microsoft Corporation*; U.S. District Court, Middle District of Florida Orlando Division; Case No. 6:20-cv-1699-PGB-DCI; 125 pages.
Exhibit B-1: "U.S. Pat. No. 8,384,771 Invalidity Chart Based On the OSIRIX 2005 System" from Defendant Microsoft Corporation's Fifth Supplemental Invalidity Contentions for *D3D Technologies. Inc.* v. *Microsoft Corporation*; U.S. District Court, Middle District of Florida Orlando Division; Case No. 6:20-cv-1699-PGB-DCI; 123 pages.
Exhibit C-1: "U.S. Pat. No. 8,384,771 Invalidity Chart Based On the Siemens 3D Prior Art System" from Defendant Microsoft Corporation's Fifth Supplemental Invalidity Contentions for *D3D Technologies. Inc.* v. *Microsoft Corporation*; U.S. District Court, Middle District of Florida Orlando Division; Case No. 6:20-cv-1699-PGB-DCI; 178 pages).

(56) References Cited

OTHER PUBLICATIONS

Exhibit A-04: "U.S. Pat. No. 8,384,771 is Anticipated by and/or Rendered Obvious In View of Tooyama" Invalidity Chart Based on Microsoft Corporation's Preliminary Invalidity Contentions for *D3D Technologies. Inc. v. Microsoft Corporation*; U.S. District Court Middle District of Florida Orlando Division; Case No. 6:20-Cv-1699-Gap-Dci; Entered Feb. 4, 2021 (115 Pages).
Exhibit A-06: "U.S. Pat. No. 8,384,771 is Anticipated by and/or Rendered Obvious In View of Kratz" Invalidity Chart Based on Microsoft Corporation's Preliminary Invalidity Contentions for *D3D Technologies. Inc. v. Microsoft Corporation*; U.S. District Court Middle District of Florida Orlando Division; Case No. 6:20-Cv-1699-Gap-Dci; Entered Feb. 4, 2021 (106 Pages).
Exhibit A-07: "U.S. Pat. No. 8,384,771 is Anticipated by and/or Rendered Obvious In View of Schoolman '952" Invalidity Chart Based on Microsoft Corporation's Preliminary Invalidity Contentions for *D3D Technologies. Inc. v. Microsoft Corporation*; U.S. District Court Middle District of Florida Orlando Division; Case No. 6:20-Cv-1699-Gap-Dci; Entered Feb. 4, 2021 (164 Pages).
Exhibit A-08: "U.S. Pat. No. 8,384,771 is Anticipated by and/or Rendered Obvious In View of Schoolman '595" Invalidity Chart Based on Microsoft Corporation's Preliminary Invalidity Contentions for *D3D Technologies. Inc. v. Microsoft Corporation*; U.S. District Court Middle District of Florida Orlando Division; Case No. 6:20-Cv-1699-Gap-Dci; Entered Feb. 4, 2021 (216 Pages).
Exhibit A-13: "U.S. Pat. No. 9,349,183 is Anticipated by and/or Rendered Obvious In View of Bauch" Invalidity Chart Based on Microsoft Corporation's Preliminary Invalidity Contentions for *D3D Technologies. Inc. v. Microsoft Corporation*; U.S. District Court Middle District of Florida Orlando Division; Case No. 6:20-Cv-1699-Gap-Dci; Entered Feb. 4, 2021 (112 Pages).
Exhibit A-02: "U.S. Pat. No. 9,349, 183 is Anticipated by and/or Rendered Obvious In View of Kniss" Invalidity Chart Based on Microsoft Corporation's Preliminary Invalidity Contentions for *D3D Technologies. Inc. v. Microsoft Corporation*; U.S. District Court Middle District of Florida Orlando Division; Case No. 6:20-Cv-1699-Gap-Dci; Entered Feb. 4, 2021 (126 Pages).
Exhibit A-02: "U.S. Pat. No. 9,349, 183 is Anticipated by and/or Rendered Obvious In View of Lima" Invalidity Chart Based on Microsoft Corporation's Preliminary Invalidity Contentions for *D3D Technologies. Inc. v. Microsoft Corporation*; U.S. District Court Middle District of Florida Orlando Division; Case No. 6:20-Cv-1699-Gap-Dci; Entered Feb. 4, 2021 (133 Pages).
Exhibit B-7: "OsiriX User Manual The Complete Reference, Revision 5.0.0 (Last Updated Apr. 24, 2017) ("User Manual")" from Defendant Microsoft Corporation's Second Supplemental Invalidity Contentions for *D3D Technologies. Inc. v. Microsoft Corporation*; U.S. District Court, Middle District of Florida Orlando Division; Case No. 6:20-cv-1699-PGB-DCI; Entered Sep. 17, 2021 (345 pages).
Exhibit B-8: "OsiriX Quick Manual, Version 1.0 ("Quick Manual")" from Defendant Microsoft Corporation's Second Supplemental Invalidity Contentions for *D3D Technologies. Inc. v. Microsoft Corporation*; U.S. District Court, Middle District of Florida Orlando Division; Case No. 6:20-cv-1699-PGB-DCI; Entered Sep. 17, 2021 (28 pages).
Exhibit B-9: "Antoine Rosset, MD et al., "OsiriX: An Open-Source Software for Navigating in Multidimensional DICOM Images" (Sep. 2004) ("Rosset")" from Defendant Microsoft Corporation's Second Supplemental Invalidity Contentions for *D3D Technologies. Inc. v. Microsoft Corporation*; U.S. District Court, Middle District of Florida Orlando Division; Case No. 6:20-cv-1699-PGB-DCI; Entered Sep. 17, 2021 (12 pages).
Exhibit A-1: "U.S. Pat. No. 8,384,771 Invalidity Chart Based On the OSIRIX 2005 System" from Defendant Microsoft Corporation's Second Supplemental Invalidity Contentions for *D3D Technologies. Inc. v. Microsoft Corporation*; U.S. District Court, Middle District of Florida Orlando Division; Case No. 6:20-cv-1699-PGB-DCI; Entered Sep. 17, 2021 (120 pages).
Exhibit B-1: "International Application No. PCT/US2007/074689 to Anderson et al., filed on Jul. 30, 2007 ("Anderson")" from Defendant Microsoft Corporation's Second Supplemental Invalidity Contentions for *D3D Technologies. Inc. v. Microsoft Corporation*; U.S. District Court, Middle District of Florida Orlando Division; Case No. 6:20-cv-1699-PGB-DCI; Entered Sep. 17, 2021 (18 pages).
Exhibit B-2: "Ronald T. Azuma, "A Survey of Augmented Reality" In Presence: Teleoperators and Virtual Environments 6, 4 (Aug. 1997) ("Azuma")" from Defendant Microsoft Corporation's Second Supplemental Invalidity Contentions for *D3D Technologies. Inc. v. Microsoft Corporation*; U.S. District Court, Middle District of Florida Orlando Division; Case No. 6:20-cv-1699-PGB-DCI; Entered Sep. 17, 2021 (48 pages).
Exhibit B-10: "U.S. Patent Publication No. 2004/0238732 A1 to State et al., issued May 11, 2010 ("State")" from Defendant Microsoft Corporation's Second Supplemental Invalidity Contentions for *D3D Technologies. Inc. v. Microsoft Corporation*; U.S. District Court, Middle District of Florida Orlando Division; Case No. 6:20-cv-1699-PGB-DCI; Entered Sep. 17, 2021 (32 pages).
IPR2021-00647 Second Declaration of Dr. Michael Zyda in *Microsoft Corporation v. D3D Technologies, Inc*; United States Patent and Trademark Office—Before the Patent Trial and Appeal Board, Case No. IPR2021-00647; Entered Feb. 23, 2022 (20 pages).
IPR2021-00647 Decision Granting Institution of inter Partes Review in *Microsoft Corporation v. D3D Technologies, Inc.*; United States Patent and Trademark Office—Before the Patent Trial and Appeal Board, Case No. IPR2021-00647; Entered Sep. 1, 2021 (31 pages).
IPR2021-00647 Declaration of Dr. Michael Zyda in *Microsoft Corporation v. D3D Technologies, Inc*; United States Patent and Trademark Office—Before the Patent Trial and Appeal Board, Case No. IPR2021-00647; Entered Mar. 11, 2021 (116 pages).

\* cited by examiner

A

B

METHOD AND APPARATUS FOR GENERATING A COLORED THREE DIMENSIONAL VOLUME VIA VOXEL ELIMINATION AND COLOR ASSIGNMENT TO VOXEL GROUPS

CROSS REFERENCE TO RELATED APPLICATIONS

This application is a Continuation of U.S. patent application Ser. No. 17/459,939, filed on Sep. 26, 2021, which is a Continuation of U.S. patent application Ser. No. 16/506,073, filed Jul. 9, 2019, now U.S. Pat. No. 11,202,061, which is a Continuation of U.S. patent application Ser. No. 15/878,463, filed Jan. 24, 2018, now U.S. Pat. No. 10,795,457, which is a Continuation-in-Part of U.S. patent application Ser. No. 14/877,442, filed Oct. 7, 2015, now U.S. Pat. No. 9,980,691, which is a Continuation-in-Part of U.S. patent application Ser. No. 12/176,569, filed Jul. 21, 2008, now U.S. Pat. No. 9,349,183, which is a Continuation-in-Part of U.S. patent application Ser. No. 11/941,578, filed Nov. 16, 2007, now U.S. Pat. No. 8,384,771, which claims the benefit of and priority under 35 U.S.C. § 119 (e) to U.S. Patent Application No. 60/877,931, filed Dec. 28, 2006, each of which are incorporated herein by reference in their entirety.

TECHNICAL FIELD

Aspects of this disclosure are generally related to radiological imaging, and more particularly to blood vessel appearance using extended reality headsets.

BACKGROUND

One of the challenges that physicians face when viewing a volume with an augmented reality, virtual reality or mixed reality headset is visualization of blood flow.

SUMMARY

All examples, aspects and features mentioned in this document can be combined in any technically possible way.

In accordance with some implementations a method of denoting blood flow within a 3D volume on a head display unit (HDU), comprises: generating a 3D volumetric dataset containing at least one blood vessel; generating at least one pointer; determining the direction of blood flow; modifying the 3D volumetric dataset by placing the at least one pointer in proximity to the at least one blood vessel in a direction aligned with a direction of blood flow; displaying, in said HDU, a left eye image based on said modified 3D volumetric dataset and a right eye image based on said modified 3D volumetric dataset, wherein said left eye image and said right eye image are alternate three-dimensional images; and displaying, in said HDU, the at least one pointer advancing in the direction of blood flow. In some implementations placing the at least one pointer in proximity to the at least one blood vessel comprises placing a 2D arrow. In some implementations placing the at least one pointer in proximity to the at least one blood vessel comprises placing a 3D arrow. Some implementations comprise displaying, in said HDU, the pointer with changing color. Some implementations comprise displaying, in said HDU, the pointer advancing in the direction of blood flow faster in arteries than veins.

DETAILED DESCRIPTION OF FIGURES

Some aspects, features and implementations described herein may include machines such as computers, electronic components, radiological components, optical components, and processes such as computer-implemented steps. It will be apparent to those of ordinary skill in the art that the computer-implemented steps may be stored as computer-executable instructions on a non-transitory computer-readable medium. Furthermore, it will be understood by those of ordinary skill in the art that the computer-executable instructions may be executed on a variety of tangible processor devices. For ease of exposition, not every step, device or component that may be part of a computer or data storage system is described herein. Those of ordinary skill in the art will recognize such steps, devices and components in view of the teachings of the present disclosure and the knowledge generally available to those of ordinary skill in the art. The corresponding machines and processes are therefore enabled and within the scope of the disclosure.

Figure 1:
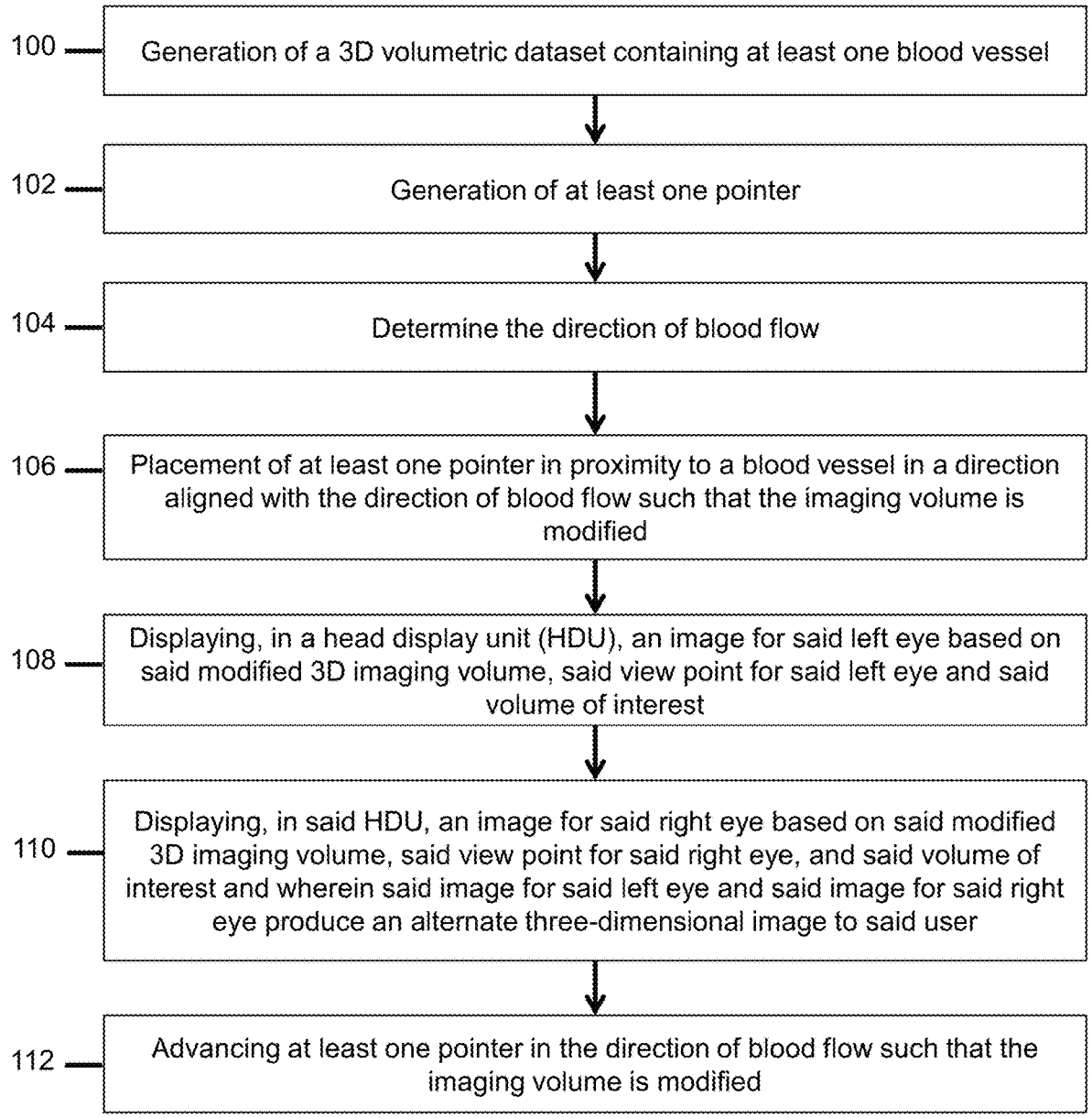
FIG. 1 illustrates the method for using pointers to denote blood flow direction within a 3D volumetric dataset and viewing with a head display unit.

FIG. 1 illustrates an implementation of a method for using pointers to denote blood flow direction within a 3D volumetric dataset and viewing with a head display unit. In the first step 100, a 3D volumetric dataset containing at least one blood vessel is generated. In the second step 102, at least one pointer is generated. In the third step 104, the direction of blood flow is determined. In the fourth step 106, at least one pointer in proximity to a blood vessel in a direction aligned with the direction of blood flow is placed such that the 3D volumetric dataset is modified. In the fifth step 108, an image for said left eye based on said modified 3D imaging volume, said view point for said left eye and said volume of interest is displayed, in the left eye display of the said HDU. In the sixth step 110, an image for said right eye based on said modified 3D imaging volume, said view point for said right eye, and said volume of interest and wherein said image for said left eye and said image for said right eye produce an alternate three-dimensional image to said user. In the seventh step 112, at least point pointer is advanced in the direction of blood flow such that the imaging volume is modified. Some portions of this process can be repeated such that multiple modified 3D imaging volumes are created and displayed on the HDU. This would serve to provide the visualization of moving arrows and help the imager better understand blood flow.

Figure 2:
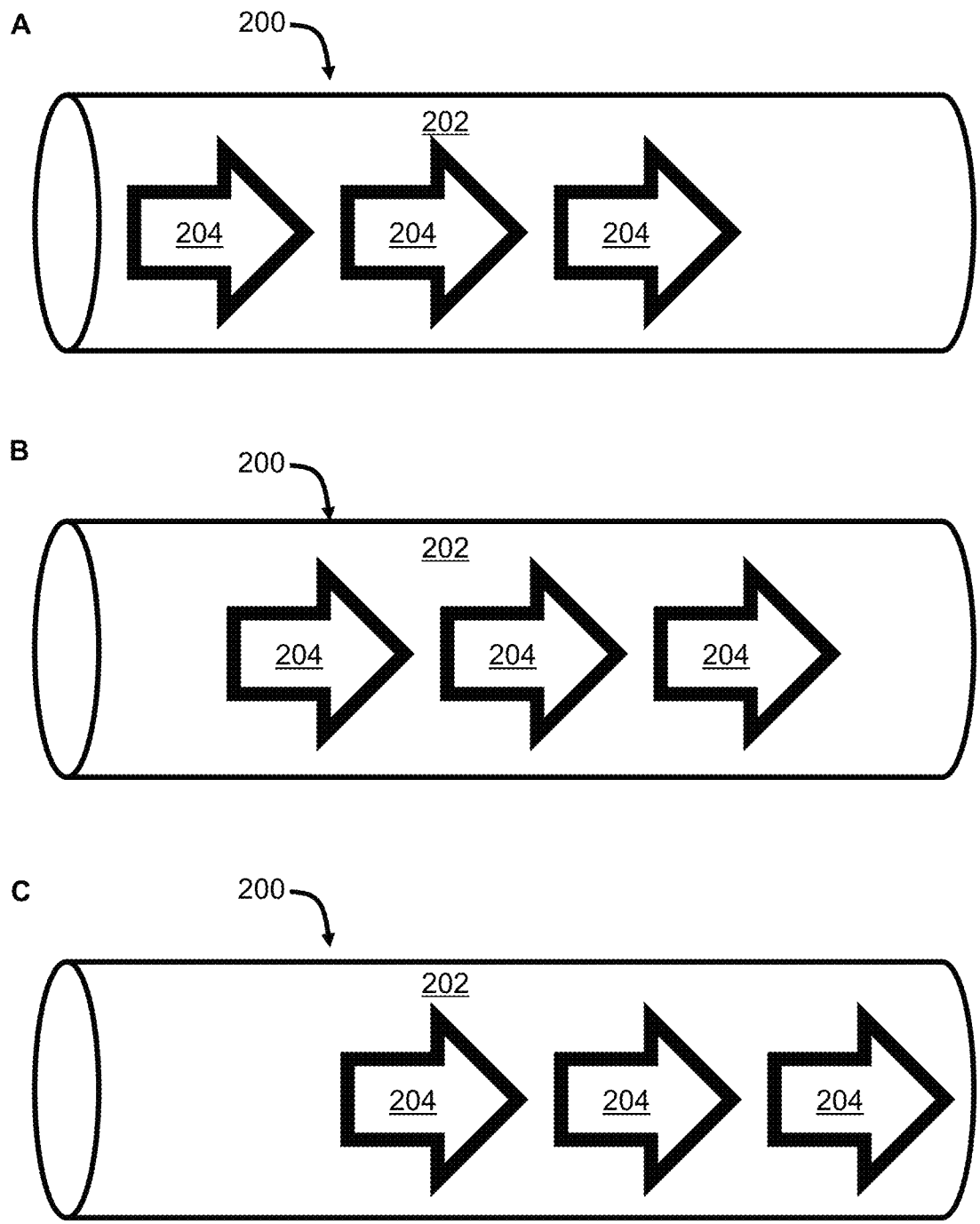
FIG. 2 illustrates advancing pointers to depict the direction of the blood flow.

FIG. 2 illustrates advancing pointers (or arrows) to depict the direction of the blood flow. In the human body, it is common for blood in most arteries to be directed away from the heart and for blood in most veins to be directed towards the heart. However, in some situations in the body (e.g., subclavian steal with retrograde flow in the vertebral artery), this rule does not apply. It can be difficult for even an experienced imager to readily determine which structures are arteries and which structures are veins. Additionally, even if an imager is able to identify a structure as an artery, it can be difficult to determine its orientation without carefully tracing it back to its origin. Through advances in computer processing, these vessels and the direction of blood flow therein can be determined. An effective visual representation method is required. In this method, advancing pointers along an artery can be performed to indicate the direction of blood flow. Similarly, advancing pointers can be performed in a vein. The color of the pointers can be changed to designate to the user whether it is an artery or vein. Further, the rate of advance of the pointers can also be varied, such as to match the natural blood flow rate for a realistic understanding of the hemodynamics of the patient. The pointers could be located in close proximity to (or within the blood vessels, such as within the center of the blood vessel). As a blood vessel curves through the 3D volume space, the path of the pointers would also curve to match that of the normal blood flow. In FIG. 2A, the pointers 204 are shown within the blood vessel lumen 202 in an initial position with respect to the blood vessel wall 200 and position of the remainder of structures within the imaging volume, which are not shown. This would represent the appearance of the imaging volume at an initial time point. In FIG. 2B, the pointers 204 are shown within the blood vessel lumen 202 in an second, slightly advanced position with respect to the blood vessel wall 200 and position of the remainder of structures within the imaging volume, which are not shown. This would represent the appearance of the imaging volume at a subsequent time point. In FIG. 2C, the pointers 204 are shown within the blood vessel lumen 202 in an third, even further advanced position with respect to the blood vessel wall 200 and position of the remainder of structures within the imaging volume, which are not shown. This would represent the appearance of the imaging volume at an additional subsequent time point. The volume that would displayed to the user on an extended reality (i.e., augmented reality, mixed reality or virtual reality headset) would therefore be dynamic and change over time. Even if the user were looking at a particular structure without moving his or her head, some items within the 3D volume would appear to be moving.

Figure 3:
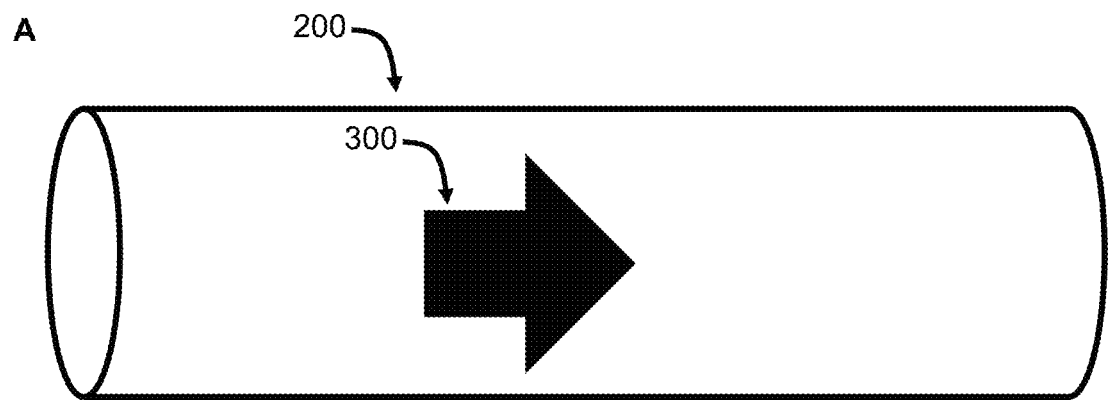
FIG. 3 illustrates placement of a 2D pointer into the 3D volume.
Figure 3:
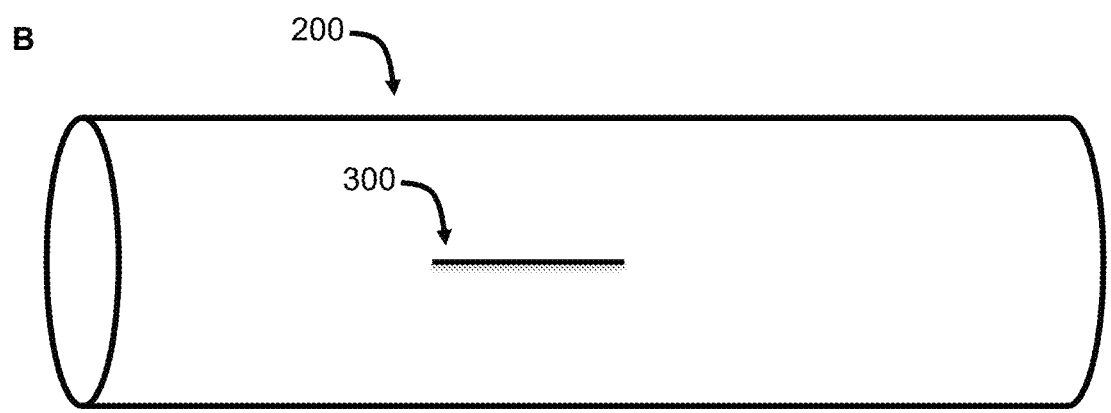

FIG. 3 illustrates placement of a 2D pointer into the 3D volume. In FIG. 3A, a 2D pointer 300 is placed into the blood vessel 200 within the 3D imaging volume. Note that this image illustrates a side view wherein the user's left and right eye view points and left and right eye viewing angles show the side of the 2D pointer 300 and the side of the blood vessel 200 within the 3D volume. In FIG. 3B, the 2D pointer 300 is placed into the blood vessel 200 within the 3D volume. Note that this image illustrates a top down view wherein the user's left and right eye view points and left and right eye viewing angles show the 2D pointer 300 and the top of the blood vessel 200 within the 3D volume. Note that since the 2D pointer is a planar slice, it nearly disappears when viewing from a near top position. A true top position with a planar 2D slice would completely disappear unless the 2D arrow was reoriented. Non-planar slices could also be used, which would be seen from any viewing angle and could be beneficial for viewing direction of blood on a curved vessel.

Figure 4:
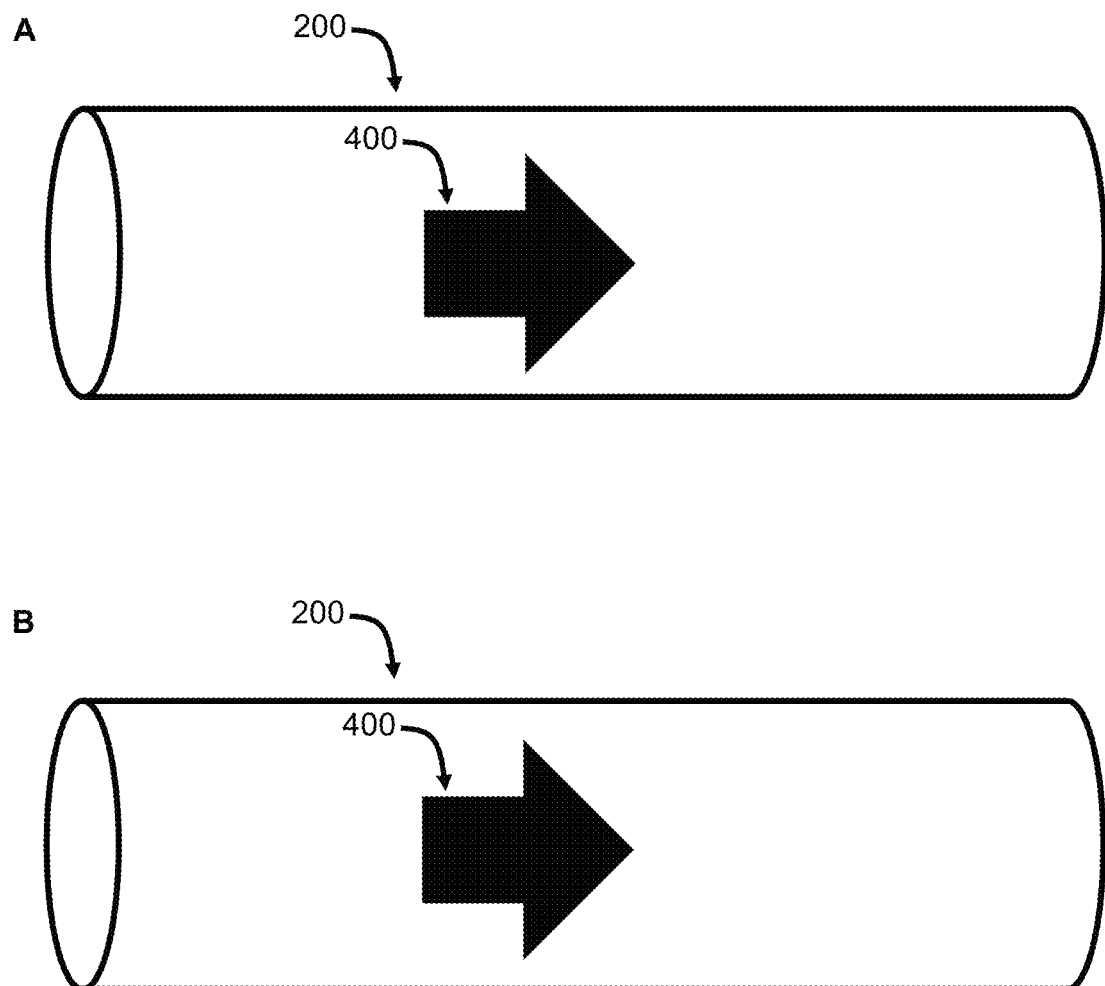
FIG. 4 illustrates placement of a 3D pointer into the 3D volume.

FIG. 4 illustrates placement of a 3D pointer into the 3D volume. In FIG. 4A, a 3D pointer 400 is placed into the blood vessel 200 within the 3D imaging volume. Note that this image illustrates a side view wherein the user's left and right eye view points and left and right eye viewing angles show the side of the 3D pointer 400 and the side of the blood vessel 200 within the 3D volume. In FIG. 4B, the 3D pointer 400 is placed into the blood vessel 200 within the 3D volume. Note that this image illustrates a top down view wherein the user's left and right eye view points and left and right eye viewing angles show the 3D pointer 400 and the top of the blood vessel 200 within the 3D volume. Note that since the pointer is 3D, it is clearly visualized when viewing from a near top position. Such a pointer could be constructed by arranging a series of 2D non-planar slices to form a cone abutting a cylinder (also made of combination of planar and non-planar slices) yielding a 3D pointer 400. By inserting this into the 3D volume, the volume would be modified.

Figure 5:
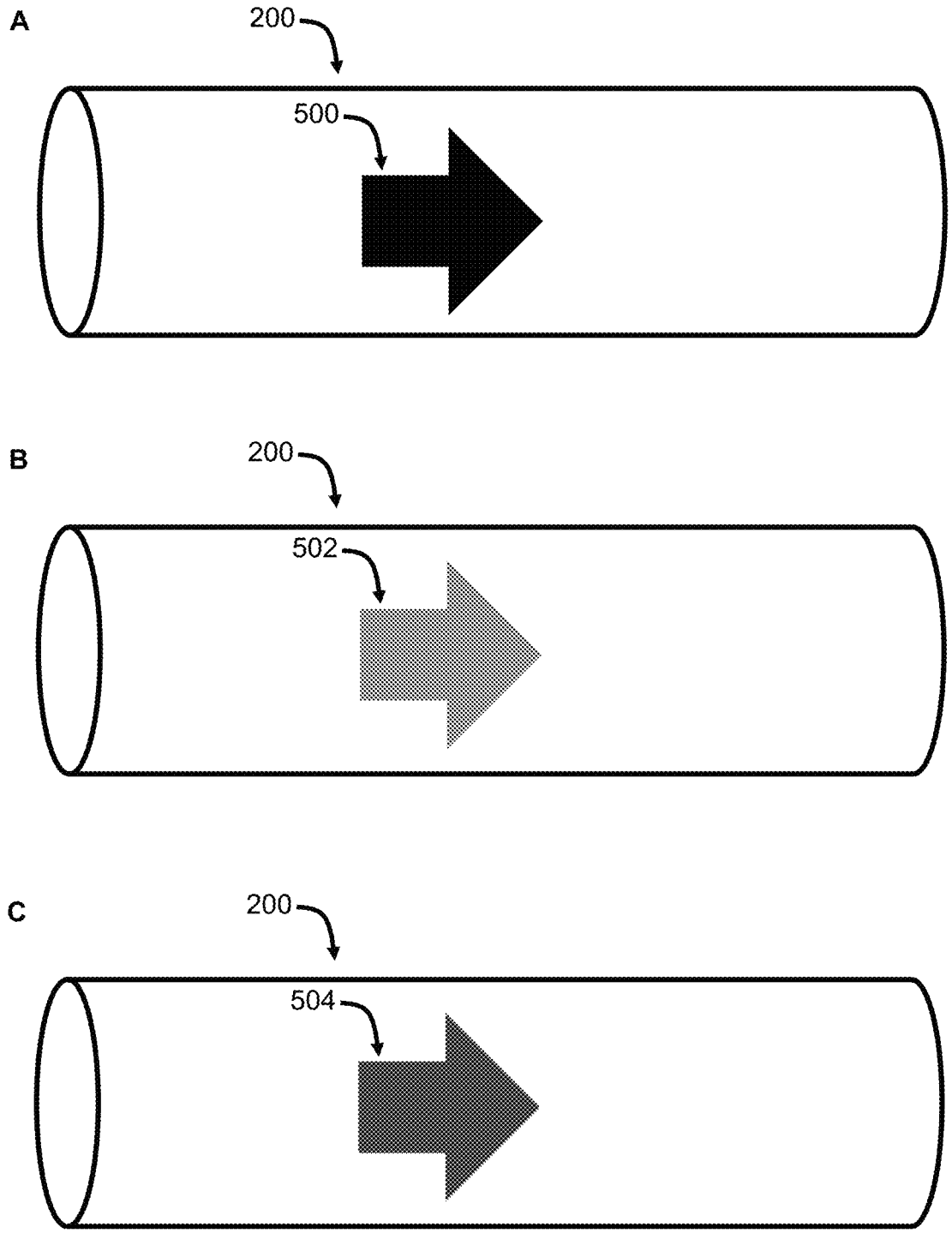
FIG. 5 illustrates placement of a 3D pointer into the 3D volume wherein the appearance of the 3D pointer can be modified.

FIG. 5 illustrates placement of a 3D pointer into the 3D volume wherein the appearance of the 3D pointer can be modified. In FIG. 5A, a 3D pointer 500 is placed into the blood vessel 200 within the 3D volume. Note that the appearance of the 3D pointer 500 is black. In FIG. 5B, the 3D pointer 502 is placed into the blood vessel 200 within the 3D volume. Note that the appearance of the 3D pointer 502 is gray. In FIG. 5C, a 3D pointer 504 is placed into the blood vessel 200 within the 3D volume. Note that the appearance of the 3D pointer 504 is red. Note that the appearance of the pointer can vary. It can be 2D or 3D. It can be a wide range of colors. It can be a wide range of shapes. It can have a wide range of textures.

Figure 6:
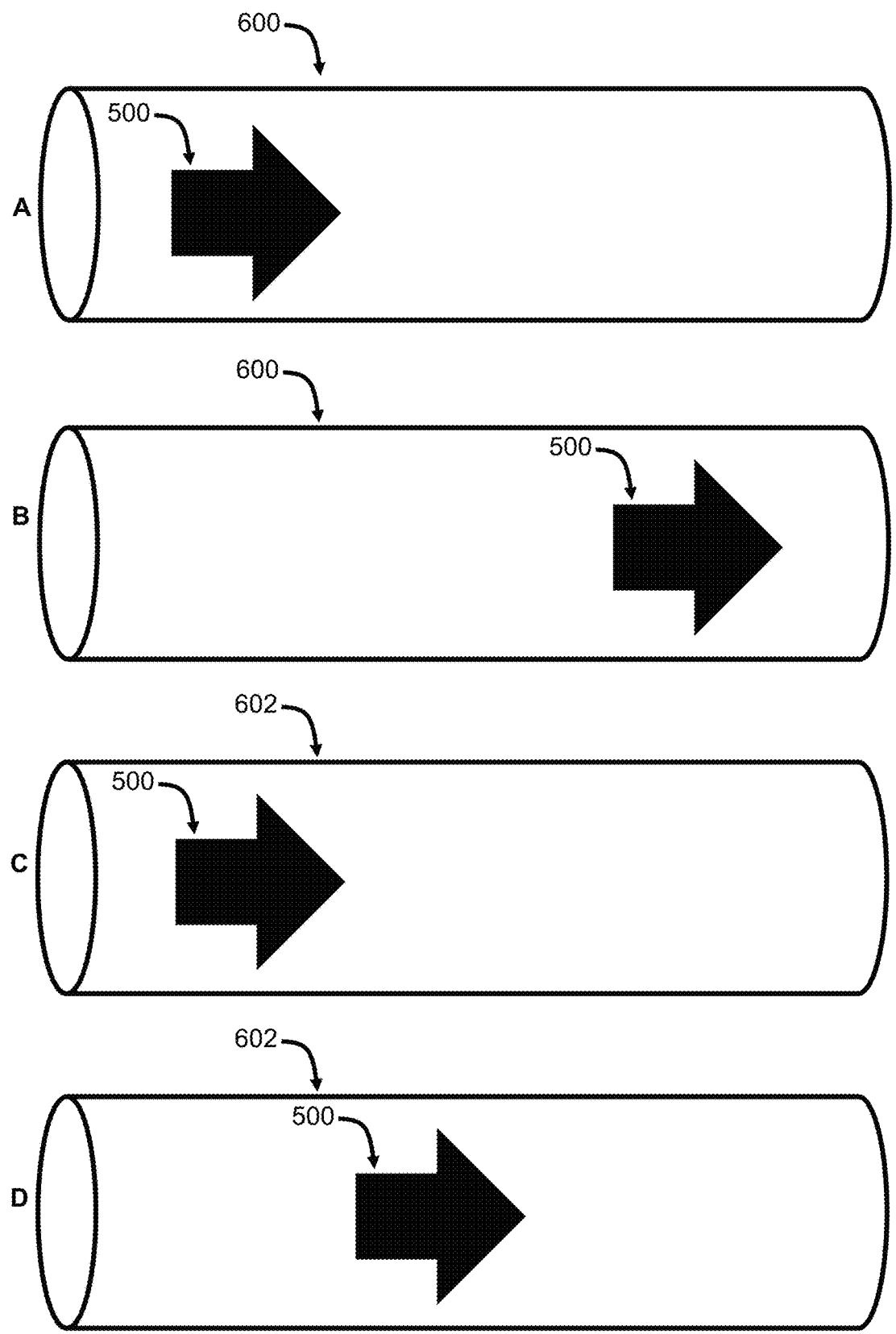
FIG. 6 illustrates variable pointer rates of movement.

FIG. 6 illustrates variable pointer rates of movement. In FIG. 6A, the black 3D pointer 500 is located within the proximal portion of an artery 600 at time point=x. In FIG. 6B, the black 3D pointer 500 has moved and is located distally towards the end of the artery 600 at time point=x+n. In FIG. 6C, the pointer 500 is located within the distal portion of a vein 602 at time point=x. In FIG. 6D, the pointer 500 is located with the mid portion of the vein 602 at time point=x+n. Note that the 3D pointer 500 is moving faster in the artery 600 as compared to the vein 602.

Several features, aspects, embodiments, and implementations have been described. Nevertheless, it will be understood that a wide variety of modifications and combinations may be made without departing from the scope of the inventive concepts described herein. Accordingly, those modifications and combinations are within the scope of the following claims.

What is claimed:

1. A computer-implemented method comprising:
    imaging a volume in response to use of an imaging device,
        wherein said imaging device uses electromagnetic energy,
        wherein said electromagnetic energy interacts with said volume, and
        wherein said volume comprises items,
    generating a 3D dataset corresponding to said volume based on said interaction,
        wherein said 3D dataset is associated with a 3D coordinate system,
        wherein said 3D dataset comprises voxels, and
        wherein each of said voxels corresponds to an intrinsic property of a corresponding item of said items;
    modifying said 3D dataset into a colored 3D dataset,
        wherein a first group of voxels of said 3D dataset is associated with a transparent volume based on an intrinsic property, and
        wherein a second group of voxels of said 3D dataset, different from the first group of voxels, is assigned a first color based on said intrinsic property to generate said colored 3D dataset,
        wherein at least one voxel of said first group of voxels resides at a first distance from a viewpoint, and at least one voxel of said second group of voxels resides at a second distance from said viewpoint, wherein said second distance is greater than said first distance; and displaying said colored 3D dataset to a user.

2. The method of claim 1 further comprising:
wherein voxels corresponding to a first numerical range of intrinsic properties are assigned a first color,
wherein voxels corresponding to a second numerical range of intrinsic properties are assigned a second color,
wherein said first numerical range is less than said second numerical range, and
wherein said first color is different from said second color.

3. The method of claim 1 further comprising:
wherein said 3D dataset is filtered, and
wherein filtering comprises elimination of voxels from said 3D dataset.

4. The method of claim 3, wherein voxels having intrinsic properties that fall in a particular numerical range are filtered.

5. The method of claim 3, wherein filtering occurs based on a voxel's location within said 3D coordinate system.

6. The method of claim 1 further comprising:
displaying, in a head display unit (HDU), a first image for a left eye based on an initial viewing angle, a first viewpoint for said left eye and said colored 3D dataset; and
displaying, in said HDU, a second image for a right eye based on said initial viewing angle, a second viewpoint for said right eye, and said colored 3D dataset,
wherein said second viewpoint is different from said first viewpoint.

7. The method of claim 6 further comprising:
using a third viewpoint for said left eye,
wherein said third viewpoint is different from said first viewpoint;
using a fourth viewpoint for said right eye,
wherein said fourth viewpoint is different from said second viewpoint, and
wherein said third viewpoint and said fourth viewpoint are different viewpoints;
displaying, in said HDU, a third image for said left eye based on said initial viewing angle, said third viewpoint for said left eye, and said colored 3D dataset; and
displaying, in said HDU, a fourth image for said right eye based on said initial viewing angle, said fourth viewpoint for said right eye, and said colored 3D dataset.

8. The method of claim 7, further comprising:
wherein said first image and said second image are based on a first convergence point,
wherein said third image and said fourth image are based on a second convergence point, and
wherein said first convergence point and said second convergence point are different.

9. The method of claim 6 further comprising:
using an alternate viewing angle of said volume of interest wherein said alternate viewing angle is different than said initial viewing angle;
displaying, in said HDU, a third image for said left eye based on said alternate viewing angle, said first viewpoint for said left eye, and said colored 3D dataset; and
displaying, in said HDU, a fourth image for said right eye based on said alternate viewing angle, said second viewpoint for said right eye, and said colored 3D dataset.

10. The method of claim 9,
wherein said first image and said second image are based on a first convergence point,
wherein said third image and said fourth image are based on a second convergence point, and
wherein said first convergence point and said second convergence point are different.

11. A computer system comprising:
a memory;
a processor;
a communications interface; and
an interconnection mechanism coupling the memory, the processor and the communications interface,
wherein the memory is encoded with an application for image processing that when executed by the processor, causes the computer system to perform the operations of:
using a 3D dataset corresponding to a volume imaged by an imaging device,
wherein said imaging device uses electromagnetic energy,
wherein said electromagnetic energy interacts with said volume,
wherein said volume comprises items,
wherein said 3D dataset is associated with a 3D coordinate system,
wherein said 3D dataset comprises voxels,
wherein each of said voxels corresponds to an intrinsic property of a corresponding item of said items;
associating a first group of voxels of said 3D dataset with a transparent volume based on intrinsic property; and
assigning to a second group of voxels of said 3D dataset, different from said first group of voxels, a first color based on said intrinsic property to generate a colored 3D dataset,
wherein at least one voxel of said first group of voxels resides at a first distance from a viewpoint, and at least one voxel of said second group of voxels resides at a second distance from said viewpoint, wherein said second distance is greater than said first distance;
and
displaying said colored 3D dataset to a user.

12. The computer system of claim 11, wherein the application, when executed by the processor, causes the computer system to perform the operations of:
assigning a first color to voxels having a first numerical range of intrinsic properties,
assigning a second color to voxels having a second numerical range of intrinsic properties,
wherein said first numerical range is less than said second numerical range, and
wherein said first color is different from said second color.

13. The computer system of claim 11, wherein the application, when executed by the processor, causes the computer system to perform the operation of:
filtering said 3D dataset,
wherein filtering comprises elimination of voxels from said 3D dataset.

14. The computer system of claim 13, wherein the application, when executed by the processor, causes the computer system to perform the operation of: filtering voxels having intrinsic properties that fall in a particular numerical range.

15. The computer system of claim 13, wherein filtering occurs based on a voxel's location within said 3D coordinate system.

16. The computer system of claim 11, wherein the application, when executed by the processor, causes the computer system to perform the operations of:
- displaying, in a head display unit (HDU), a first image for a left eye based on an initial viewing angle, a first viewpoint for said left eye and said colored 3D dataset; and
- displaying, in said HDU, a second image for a right eye based on said initial viewing angle, a second viewpoint for said right eye, and said colored 3D dataset, and
- wherein said second viewpoint is different from said first viewpoint.

17. The computer system of claim 16, wherein the application, when executed by the processor, causes the computer system to perform the operations of:
- using a third viewpoint for said left eye,
  - wherein said third viewpoint is different from said first viewpoint;
- using a fourth viewpoint for said right eye,
  - wherein said fourth viewpoint is different from said second viewpoint, and
  - wherein said third viewpoint and said fourth viewpoint are different viewpoints;
- displaying, in said HDU, a third image for said left eye based on said initial viewing angle, said third viewpoint for said left eye, and said colored 3D dataset; and
- displaying, in said HDU, a fourth image for said right eye based on said initial viewing angle, said fourth viewpoint for said right eye, and said colored 3D dataset.

18. The computer system of claim 17,
- wherein said first image and said second image are based on a first convergence point,
- wherein said third image and said fourth image are based on a second convergence point, and
- wherein said first convergence point and said second convergence point are different.

19. The computer system of claim 16, wherein the application, when executed by the processor, causes the computer system to perform the operations of:
- using an alternate viewing angle of said volume of interest wherein said alternate viewing angle is different than said initial viewing angle;
- displaying, in said HDU, a third image for said left eye based on said alternate viewing angle, said first viewpoint for said left eye, and said colored 3D dataset; and
- displaying, in said HDU, a fourth image for said right eye based on said alternate viewing angle, said second viewpoint for said right eye, and said colored 3D dataset.

20. The computer system of claim 19,
- wherein said first image and said second image are based on a first convergence point,
- wherein said third image and said fourth image are based on a second convergence point, and
- wherein said first convergence point and said second convergence point are different.

21. One or more non-transitory computer readable media storing instructions that, when executed, cause:
- accessing a 3D dataset corresponding to a volume imaged by an imaging device,
  - wherein said volume comprises items,
  - wherein said 3D dataset is associated with a 3D coordinate system,
  - wherein said 3D dataset represents voxels, and
  - wherein each of said voxels corresponds to an intrinsic property of a corresponding item of said items;
- associating a first group of voxels of said 3D dataset with a transparent volume based on intrinsic property; and
- assigning to a second group of voxels of said 3D dataset, different from said first group of voxels, a first color based on said intrinsic property to generate a colored 3D dataset,
- wherein at least one voxel of said first group of voxels resides at a first distance from a viewpoint, and at least one voxel of said second group of voxels resides at a second distance from said viewpoint, wherein said second distance is greater than said first distance.

22. The one or more non-transitory computer readable media of claim 21, further storing instructions that, when executed, cause display of said colored 3D dataset.

23. The method of claim 1, wherein said intrinsic property corresponds to a signal intensity.

24. The system of claim 11, wherein said intrinsic property corresponds to a signal intensity.

25. The one or more non-transitory computer readable media of claim 21, wherein said intrinsic property corresponds to a signal intensity.

26. The one or more non-transitory computer readable media of claim 21, wherein said first distance corresponds to a surface of said volume, and said second distance corresponds to an interior of said volume.

27. The one or more non-transitory computer readable media of claim 21, wherein said at least one voxel of said first group resides along a ray between said viewpoint and said at least one voxel of said second group.

28. The one or more non-transitory computer readable media of claim 21, wherein said second group of voxels is assigned said first color based on a first range of values of said intrinsic property, and said first group of voxels is associated with a transparent volume based on at least one value of said intrinsic property outside said first range.

* * * * *